(12) United States Patent
Mane et al.

(10) Patent No.: US 10,040,776 B2
(45) Date of Patent: Aug. 7, 2018

(54) PYRAN DERIVATIVES AND THEIR PREPARATION

(71) Applicant: V. MANE FILS, Bar sur Loup (FR)

(72) Inventors: Jean Mane, Grasse (FR); Caroline Plessis, Chateauneuf (FR); Jean-Jacques Chanot, Speracedes (FR)

(73) Assignee: V. MANE FILS, Bar sur Loup (FR)

( * ) Notice: Subject to any disclaimer, the term of this patent is extended or adjusted under 35 U.S.C. 154(b) by 0 days.

(21) Appl. No.: 15/448,006

(22) Filed: Mar. 2, 2017

(65) Prior Publication Data

US 2017/0174647 A1 Jun. 22, 2017

Related U.S. Application Data

(62) Division of application No. 12/988,704, filed as application No. PCT/EP2009/054691 on Apr. 21, 2009, now Pat. No. 9,593,092.

(30) Foreign Application Priority Data

Apr. 22, 2008 (EP) .................................... 08305118

(51) Int. Cl.
| | | |
|---|---|---|
| *C07D 309/12* | (2006.01) | |
| *A23L 33/10* | (2016.01) | |
| *C11B 9/00* | (2006.01) | |
| *A61K 8/49* | (2006.01) | |
| *A61Q 13/00* | (2006.01) | |

(52) U.S. Cl.
CPC ............ *C07D 309/12* (2013.01); *A23L 33/10* (2016.08); *A61K 8/498* (2013.01); *A61Q 13/00* (2013.01); *C11B 9/008* (2013.01); *A23V 2002/00* (2013.01)

(58) Field of Classification Search
CPC ....... C07D 309/12; A23L 33/10; C11B 9/008; A61K 8/498; A61Q 13/00; A23V 2002/00
See application file for complete search history.

(56) References Cited

U.S. PATENT DOCUMENTS

2005/0004210 A1* 1/2005 Umada ................ C07D 309/08
514/460

FOREIGN PATENT DOCUMENTS

EP 0383446 A2 * 8/1990

\* cited by examiner

*Primary Examiner* — John M Mauro
(74) *Attorney, Agent, or Firm* — B. Aaron Schulman, Esq.; Stites & Harbison, PLLC

(57) ABSTRACT

A compound of formula (I)

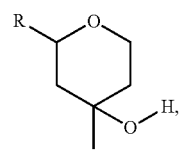

(I)

is provided wherein R represents a linear or branched C5 alkyl group, as well as the use of such compounds in a fragrant and/or flavoring composition, or as a masking agent for odors and/or flavors.

5 Claims, No Drawings

PYRAN DERIVATIVES AND THEIR PREPARATION

CROSS REFERENCE TO RELATED APPLICATIONS

This application is a divisional application of U.S. Ser. No. 12/988,704, having a filing date of Jan. 3, 2011, and issued on Mar. 14, 2017, as U.S. Pat. No. 9,593,092, which was a 371 application of International application PCT/EP2009/054691, filed Apr. 21, 2009, which claimed the benefit of European Patent application EP 08305118.5, filed Apr. 22, 2008, all of said applications incorporated herein by reference.

FIELD OF THE INVENTION

The present invention relates to the field of fragrances and flavours. More particularly, the invention relates to new pyran derivatives, their method of preparation, and their use in the fields of perfumery and flavouring.

BACKGROUND OF THE INVENTION

Tetrahydropyrans and dihydropyrans belong to an important class of fragrant ingredients and much work has already been done to prepare known compounds, such as Rose Oxide and similar derivatives, from linear or branched alkyl and alkenyl aldehydes as described in U.S. Pat. No. 3,681,263 and WO 04/009749, or from benzylic aldehydes as described in CH 655 932.

Similarly, pyranols as well as their ester or ether derivatives have also found themselves interests in the aromatic industry as shown in U.S. Pat. No. 4,963,285 and U.S. Pat. No. 4,962,090.

Developing new fragrant pyran derivatives is a huge challenge, since such compounds blend well with other fragrant ingredients, and have good stability in any sort of perfumed bases, used for cosmetics, household products, etc.

In terms of the problem to be solved, the Applicant thus focused on the preparation of new pyran derivatives.

The need for new compounds is of great importance for the development of the fragrance industry, which recently had to face stricter international regulatory requirements about the use of certain materials, as well as environmental concerns and customer demands for improved performance. Developing new fragrant and/or flavouring compounds is also important for providing alternatives to already existing fragrant and/or flavouring compounds so as to minimize the risk of allergies due to repeated exposure to the same compounds. Providing new fragrant and/or flavouring compounds as well as means of manufacturing such compounds, is therefore an object of the invention.

In other words, it is an aim of the present invention to provide a new process of manufacturing fragrant compounds, as well as such compounds.

SUMMARY OF THE INVENTION

The invention is directed to a process of preparation of compounds of formula (I)

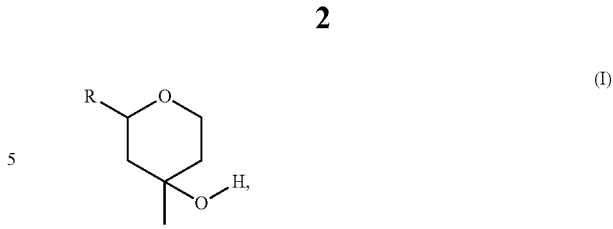

wherein R represents a linear or branched C5 alkyl group, the process comprising reacting a compound of formula (III)

wherein R is as defined in respect of formula (I), with a compound of formula (IV)

in the presence of an acid. The reaction is carried out in an organic solvent selected from the group comprising toluene, xylene, trimethylbenzene, cyclohexane, and methylcyclohexane, at a temperature of about 70° C. to reflux, preferably at 80° C. to 90° C., and even more preferably at about 80° C., so as to obtain a compound of formula (I).

The invention includes all isomers of the compounds of formula (I).

DETAILED DESCRIPTION OF EXEMPLARY EMBODIMENTS

In a preferred embodiment the compound of formula (III) is selected from the group comprising 2-ethyl-butyraldehyde and hexanal.

The acid is preferably selected from the group comprising p-toluenesulfonic acid (PTSA), $H_2SO_4$, and supported acids, in particular acids supported on ion exchange resins or on clays. Particularly preferred supported acids are $H_2SO_4$, sulfonic acid, and $ZnCl_2$ supported on clay, such as montmorillonite, or on an ion exchange resin. Examples of suitable supported catalysts include $H_2SO_4$ supported on ion exchange resin, marketed for example under the trade name AMBERLYST® 15; sulfonic acid supported on montmorillonite, marketed under the trade name Montmorillonite KSF; and $ZnCl_2$ supported on montmorillonite, marketed under the trade name Montmorillonite K10. The main advantage of supported acids is that they are easy to use, in particular in view of their separation from the reaction product. Furthermore, certain acids such as for example AMBERLYST® 15, may be used during several cycles before a loss of activity appears.

Supported acids are advantageously used in an amount of 5 to 50%, preferably 10 to 30%, and even more preferably about 10% by weight of the weight of compound (III).

Non-supported acids, such as p-toluenesulfonic acid (PTSA) and $H_2SO_4$ are advantageously used in an amount of 1 to 10%, preferably 2 to 5%, and even more preferably about 5% by weight of the weight of compound (III).

The acid may also be a halogenated carboxylic acid or a mixture of a carboxylic acid and a halogenated carboxylic acid. A preferred carboxylic acid is acetic acid and a preferred halogenated carboxylic acid is trifluoroacetic acid. When used as a mixture, the molar ratio of carboxylic acid/halogenated carboxylic acid, in particular of acetic acid/trifluoroacetic acid is comprised between 0:100 and 99:1, preferably between 50:50 and 95:5 and even more preferably, the molar ratio is about 85:15. The main advantage of using a mixture of a carboxylic acid and halogenated carboxylic acid, instead of the sole halogenated carboxylic acid, is the reduction of costs. The more halogenated carboxylic acid is replaced by a carboxylic acid, the more the process is interesting from an economic point of view.

When the acid is a halogenated carboxylic acid or a mixture of a carboxylic acid and a halogenated carboxylic acid, the process of the invention further comprises a step of saponification, so as to obtain a pyranol of formula (I).

In an advantageous aspect of the invention, the reaction of compounds (III) and (IV) is carried out during 1 to 48 hours, preferably 1 to 8 hours, and even more preferably about 2 hours.

The process of the invention allows the preparation of compounds of formula (I) in good yields. Preferred compounds of formula (I) are those wherein R is selected from the group consisting of 1-pentyl, 2-pentyl, 3-pentyl (1-ethyl-propyl), 1-(2-methyl-butyl), 2-(2-methyl-butyl), 2-(3-methyl-butyl), 1-(3-methyl-butyl), and 1-(2,2-dimethyl)-propyl. Novel compounds of formula (Ia). Particularly preferred compounds of formula (I) are 2-(1-ethyl-propyl)-4-methyl-tetrahydro-2H-pyran-4-ol, and 2-(1-pentyl)-4-methyl-tetrahydro-2H-pyran-4-ol.

In a variant of the process of the invention, the process further comprises a step of reacting the compound of formula (I) with
an acid anhydride of formula (V)

 (V), or an acyl halogenide of formula (VI)

 (VI), wherein R' is a carbonyl group substituted with a hydrogen or a linear or branched C1-C6 alkyl group or a linear or branched C2-C6 alkenyl group, so as to obtain a compound of formula (Ia)

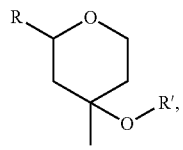

wherein R is as defined in respect of formula (I), and R' is as defined in respect of formulae (V) and (VI).

Preferably R' is selected from the group consisting of acetyl, propionyl, crotonyl (but-2-enoyl), 2-methyl-but-2-enoyl, butyryl, iso-butyryl, 2-methyl-butyryl, valeryl, iso-valeryl, 2-methyl-valeryl, 3-methyl-valeryl, hexenoyl, hex-3-enoyl.

Preferred compounds of formula (Ia) are 2-(1-ethyl-propyl)-4-methyl-tetrahydro-2H-pyran-4-yl acetate, propionic acid 2-(1-ethyl-propyl)-4-methyl-tetrahydro-2H-pyran-4-yl ester, but-2-enoic acid 2-(1-ethyl-propyl)-4-methyl-tetrahydro-2H-pyran-4-yl ester, but-3-enoic acid 2-(1-ethyl-propyl)-4-methyl-tetrahydro-2H-pyran-4-yl ester, and 4-methyl-2-(1-pentyl)-tetrahydro-2H-pyran-4-yl acetate.

The esterification is carried out according to methods known in the art.

The process according to the invention may comprise between the cyclisation and the esterification a purification step of the compound of formula (I). However, the esterification may also be carried out with the crude pyranol of formula (I). The intermediate purification is particularly advantageous if the reaction mixture contains by-products which are difficult to separate from the final ester, but which may be more easily separated from the pyranol of formula (I).

In another aspect of the invention, the process further comprises dehydrating the compound of formula (I) so as to obtain a compound of formula (II)

wherein R is as defined in respect of formula (I), and the dotted lines represent a double bond involving the carbon atom at the 4 position.

The dehydration is advantageously carried out in a solvent selected from the group consisting of toluene, xylene, trimethylbenzene, cyclohexane, and methylcyclohexane. It is preferably carried out in the same solvent as the preparation of compound (I). The reaction is carried out at a temperature of about 70° C. to reflux, preferably at refluxing temperature.

In still another aspect of the invention the process comprises, after dehydrating the compound of (I) so as to obtain a compound of formula (II), a step of hydrogenating compound (II) so as to obtain the corresponding 4-methyl-tetrahydropyran of formula (II')

The hydrogenation is carried out according to any suitable hydrogenation method known in the art. A suitable method is hydrogenation in the presence of Pd (palladium) on charcoal.

The invention is also directed to compounds of formula (II) and

wherein R is selected from the group consisting of 3-pentyl, 1-(2-methyl-butyl), 2-(2-methyl-butyl), 2-(3-methyl-butyl), and 1-(2,2-dimethyl)-propyl, and the dotted lines represent a double bond involving the carbon atom at the 4 position. Compounds of formula (II) are hence

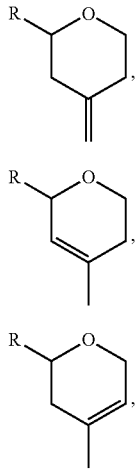

wherein R is as defined in respect of general formula (II).

Preferred compounds of formula (II) are selected among 4-methylene-2-(3-pentyl)-tetrahydro-2H-pyran, 4-methyl-2-(3-pentyl)-5,6-dihydro-2H-pyran, 4-methyl-2-(3-pentyl)-3,6-dihydro-2H-pyran, 4-methylene-2-(1-pentyl)-tetrahydro-2H-pyran, 4-methyl-2-(1-pentyl)-5,6-dihydro-2H-pyran, 4-methyl-2-(1-pentyl)-3,6-dihydro-2H-pyran.

The invention is further directed to compounds of formula (II')

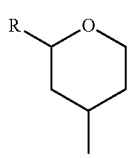

wherein R represents a linear or branched C5 alkyl group, preferably a group selected from the group consisting of 1-pentyl, 2-pentyl, 3-pentyl (1-ethyl-propyl), 1-(2-methyl-butyl), 2-(2-methyl-butyl), 2-(3-methyl-butyl), 1-(3-methyl-butyl), and 1-(2,2-dimethyl)-propyl.

Selected novel compounds of formulae (I) and (Ia) are another object of the invention. Novel compounds of formula (I)

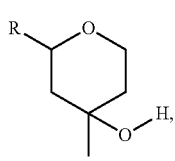

are those wherein R is selected from the group consisting of 3-pentyl, (1-ethyl-propyl), 1-(2-methyl-butyl), 2-(2-methyl-butyl), 2-(3-methyl-butyl), 1-(3-methyl-butyl), and 1-(2,2-dimethyl)-propyl. Particularly preferred compounds of formula (I) is 2-(1-ethyl-propyl)-4-methyl-tetrahydro-2H-pyran-4-ol.

Novel compounds of formula (Ia)

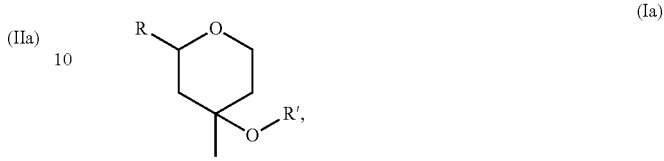

are those wherein R is selected from the group consisting of 1-pentyl, 3-pentyl, 1-(2-methyl-butyl), 2-(2-methyl-butyl), 2-(3-methyl-butyl), 1-(3-methyl-butyl), and 1-(2,2-dimethyl)-propyl and R' is a carbonyl group substituted with a hydrogen atom or a linear or branched C1-C6 alkyl group or a linear or branched C2-C6 alkenyl group. Preferably R' is selected from the group consisting of acetyl, propionyl, crotonyl (but-2-enoyl), 2-methyl-but-2-enoyl, butyryl, iso-butyryl, 2-methyl-butyryl, valeryl, iso-valeryl, 2-methyl-valeryl, 3-methyl-valeryl, hexenoyl, and hex-3-enoyl. Particularly preferred compounds of formula (Ia) are 2-(1-ethyl-propyl)-4-methyl-tetrahydro-2H-pyran-4-yl acetate, propionic acid 2-(1-ethyl-propyl)-4-methyl-tetrahydro-2H-pyran-4-yl ester, but-2-enoic acid 2-(1-ethyl-propyl)-4-methyl-tetrahydro-2H-pyran-4-yl ester, but-3-enoic acid 2-(1-ethyl-propyl)-4-methyl-tetrahydro-2H-pyran-4-yl ester, and 4-methyl-2-(1-pentyl)-tetrahydro-2H-pyran-4-yl acetate.

The compounds of the invention exhibit interesting olfactive properties. Particularly, in comparison to Florol (2-isobutyl-4-methyl-tetrahydro-2H-pyran-4-ol), even though 2-(1-ethyl-propyl)-4-methyl-tetrahydro-2H-pyran-4-ol shows a less intensive starting odour, the note lasts longer, and blends very well in floral composition to enhance (boost) other top note compounds. The compounds of the invention are therefore of particular interest in the field of perfumery.

A further object of the invention is thus the use of a compound of formula (I), wherein R is selected from the group consisting of 3-pentyl (1-ethyl-propyl), 1-(2-methyl-butyl), 2-(2-methyl-butyl), 2-(3-methyl-butyl), 1-(3-methyl-butyl), and 1-(2,2-dimethyl)-propyl; of formula (Ia), wherein R is selected from the group consisting of 1-pentyl, 3-pentyl, 1-(2-methyl-butyl), 2-(2-methyl-butyl), 2-(3-methyl-butyl), 1-(3-methyl-butyl), and 1-(2,2-dimethyl)-propyl and R' is a carbonyl group substituted with a hydrogen atom or a linear or branched C1-C6 alkyl group or a linear or branched C2-C6 alkenyl group; of formula (II), wherein R is linear or branched C5 alkyl, and the dotted lines represent a double bond involving the carbon atom at the 4 position; or of formula (II'), wherein R is linear or branched C5 alkyl, in the field of perfumery, for the preparation of perfumed bases and concentrates, fragrances, perfumes; topic compositions; cosmetic compositions, such as face and body creams, cleansers, facial treatments, talc powders, hair oils, shampoos, hair lotions, bath oils and salts, shower and bath gels, soaps, body anti-perspirants and deodorizers, pre-shave, shaving and post-shave creams and lotions, creams, toothpastes, mouth baths, pomades; and cleaning products, such as softeners, detergents, air deodorizers and household cleaning supplies.

The invention is also directed to the use of a compound of formula (I), wherein R is selected from the group consisting of 3-pentyl (1-ethyl-propyl), 1-(2-methyl-butyl), 2-(2-methyl-butyl), 2-(3-methyl-butyl), 1-(3-methyl-butyl), and 1-(2,2-dimethyl)-propyl; of formula (Ia), wherein R is selected from the group consisting of 1-pentyl, 3-pentyl, 1-(2-methyl-butyl), 2-(2-methyl-butyl), 2-(3-methyl-butyl), 1-(3-methyl-butyl), and 1-(2,2-dimethyl)-propyl and R' is a carbonyl group substituted with a hydrogen atom or a linear or branched C1-C6 alkyl group or a linear or branched C2-C6 alkenyl group; of formula (II), wherein R is linear or branched C5 alkyl, and the dotted lines represent a double bond involving the carbon atom at the 4 position; or of formula (II'), wherein R is linear or branched C5 alkyl, as flavouring agent for the preparation of foodstuffs, drinks, and tobacco. The foodstuffs and drinks are preferably selected from the group consisting of dairy products, ice creams, soups, sauces, dips, dishes, meat products, culinary assistances, salted biscuits, snacks, soft drinks, beers, wines and spirits.

The invention is also directed to the use of a compound of formula (I), wherein R is selected from the group consisting of 3-pentyl (1-ethyl-propyl), 1-(2-methyl-butyl), 2-(2-methyl-butyl), 2-(3-methyl-butyl), 1-(3-methyl-butyl), and 1-(2,2-dimethyl)-propyl; of formula (Ia), wherein R is selected from the group consisting of 1-pentyl, 3-pentyl, 1-(2-methyl-butyl), 2-(2-methyl-butyl), 2-(3-methyl-butyl), 1-(3-methyl-butyl), and 1-(2,2-dimethyl)-propyl and R' is a carbonyl group substituted with a hydrogen atom or a linear or branched C1-C6 alkyl group or a linear or branched C2-C6 alkenyl group; of formula (II), wherein R is linear or branched C5 alkyl, and the dotted lines represent a double bond involving the carbon atom at the 4 position; or of formula (II'), wherein R is linear or branched C5 alkyl, as masking agent of odours and/or flavours, e.g. in pharmaceutical, cosmetic or food compositions.

The invention also provides the use of a compound of formula (I), wherein R is selected from the group consisting of 3-pentyl (1-ethyl-propyl), 1-(2-methyl-butyl), 2-(2-methyl-butyl), 2-(3-methyl-butyl), 1-(3-methyl-butyl), and 1-(2,2-dimethyl)-propyl; of formula (Ia), wherein R is selected from the group consisting of 1-pentyl, 3-pentyl, 1-(2-methyl-butyl), 2-(2-methyl-butyl), 2-(3-methyl-butyl), 1-(3-methyl-butyl), and 1-(2,2-dimethyl)-propyl and R' is a carbonyl group substituted with a hydrogen atom or a linear or branched C1-C6 alkyl group or a linear or branched C2-C6 alkenyl group; of formula (II), wherein R is linear or branched C5 alkyl, and the dotted lines represent a double bond involving the carbon atom at the 4 position; or of formula (II'), wherein R is linear or branched C5 alkyl, in combination with other perfuming or flavouring ingredients, solvents or additives or fixatives.

The compounds of the invention may be used in a concentration comprised in a range from 0.001% to 99% in weight, preferably from 0.1% to 50% in weight, more preferably from 0.1% to 30% in weight. It is known by the man skilled in the art that these values depend on the nature of the composition/article to be perfumed and/or flavoured, the desired intensity of the perfume and/or flavour, and of the nature of the other ingredients present in said composition or article. According to a preferred embodiment of the invention, compounds are used in an olfactory effective amount.

Definitions

The terms "fragrance" and "fragrant", as used herein, are used interchangeably whenever a compound or a mixture of compounds is referred to, which is intended to pleasantly stimulate the sense of smell.

The terms "flavour" and "flavouring", as used herein, are used interchangeably whenever a compound or a mixture of compounds is referred to, which is intended to stimulate the sense of taste and smell. Also in the meaning of the invention, the term "flavouring" relates to the flavouring of any liquid or solid, human or animal, in particular of drinks, dairy products, ice creams, soups, sauces, dips, dishes, meat products, culinary assistances, salted biscuits or snacks. It also means the flavouring of beers, wines and tobaccos.

The term "olfactory effective amount", as used herein, means a level or amount of fragrant/flavouring compound present in a material at which the incorporated compound exhibits a sensory effect.

By the term "masking" is meant reducing or eliminating malodour or bad flavour perception generated by one or more molecules entering in the composition of a product.

The term "isomer", in the present invention, means molecules having the same chemical formula, which means same number and types of atoms, but in which the atoms are arranged differently. The term "isomer" includes structural isomers, geometric isomers, optical isomers and stereoisomers. It particularly includes the cis/trans isomers of the compounds of formulae (I) and (Ia), the cis isomer being the one where R and the hydroxyl group are both on the same side of the cycle and the trans configuration being the one where R and the hydroxyl group are on a different side of the cycle.

The term "linear or branched C5 alkyl group" comprises all alkyl groups having five carbon atoms. Linear C5 alkyl is 1-pentyl. Branched C5 alkyl groups are 2-pentyl, 3-pentyl, 1-(2-methyl-butyl), 2-(2-methyl-butyl), 2-(3-methyl-butyl), 1-(3-methyl-butyl), and 1-(2,2-dimethyl)-propyl.

EXAMPLES

The present invention will be better understood with reference to the following examples. These examples are intended to representative of specific embodiments of the invention, and are not intended as limiting the scope of the invention.

Example 1: Preparation of 2-(1-ethyl-propyl)-4-methyl-tetrahydro-2H-pyran-4-ol

A 2M solution of 2-ethyl-butyraldehyde (1 eq.) and 3-methyl-3-buten-1-ol (1 eq.) in toluene with 10% weight of Montmorillonite K10 is heated under reflux or at 80° C. for 2 hours. After cooling down, the mixture is filtered on a frit and the solvents are evaporated. The crude mixture is then distilled with a Vigreux column under reduced pressure. To get a purer compound, a fine distillation with a packed column can be also performed.

The results are summarised in the table below.

| Conditions Fractions | Temp. of reaction: reflux 2-ethyl-butyraldehyde: 200 g (2 mol) 385 g crude product (Pyrans 33%, pyranols 51%, ethers 9%) Crude yield (pyranols) = 53% | | Temp. of reaction: 80° C. 2-ethyl-butyraldehyde: 21 g (0.21 mol) 37.6 g crude product (Pyrans 11%, pyranols 67%, ethers 15%) Crude yield (pyranols) = 64% | | Temp. of reaction: 80° C. 2-ethyl-butyraldehyde: 100 g (1 mol) 205 g crude product (Pyrans 15%, pyranols 58%, ethers 18%) Crude yield (pyranols) = 64% | |
|---|---|---|---|---|---|---|
| | Bp | Mass/ Product(s) | Bp | Mass/ Product(s) | Bp | Mass/ Product(s) |
| I | 77-80° C./ 1 kPa | 80 g Pyrans (90% purity) | → 68° C./ 800 Pa | 5 g Pyrans (54%) Pyranols (35.7%) | → 60° C./ 667 Pa | 8.6 g Pyrans (54%) Pyranols (35.7%) |
| II | 85-100° C./ 1 kPa | 79 g Pyrans (26%) Pyranols (67%) | 75-90° C./ 667 Pa | 18.2 g Pyranols (93% purity) | 96-98° C./ 667 Pa | 87 g Pyranols (95% purity) |
| III | 105° C./ 800 Pa | 104 g Pyranols (90%; purity) | 105° C./ 667 Pa | 5.2 g Pyranols (41%) Pyranyl ethers (54%) | 109-115° C./ 667 Pa | 7.5 g Pyranols (73%) Pyranyl ethers (22%) |

The 2-(1-ethyl-propyl)-4-methyl-tetrahydro-pyran-4-ol thus obtained is usually a 50:50 mixture of cis/trans isomers.

Odour: Top notes: Green, floral, Lily of the valley, rosy, Rose oxide.

Dried down notes: Lily of the valley, lemony, musky.

Tenacity on the blotter: 48 hours; more than Rose oxide.

IR (film, cm-1): 592w, 633w, 882w, 936w, 1005w, 1059w, 1083m, 1107m, 1127m, 1166m, 1257w, 1346w, 1379m, 1464m, 2876s, 2963s, 3407 (br)m.

1$^{st}$ Isomer:

$^1$H-NMR (200 MHz, CDCl$_3$): δ (ppm) 0.86 (t, J=7.1 Hz, 6H); 1.18-1.74 (m, 9H); 1.25 (s, 3H); 3.58 (ddd, J=2.4 Hz, J=5.2 Hz, J=11.3 Hz, 1H); 3.71 (dt, J=2.5 Hz, J=11.9 Hz, 1H); 3.75-3.90 (m, 1H).

$^{13}$C-NMR (50 MHz, CDCl$_3$): δ (ppm) 11.50 & 11.55; 21.46; 32.01; 38.86; 41.11; 45.65; 63.80; 68.06; 74.40.

MS [e/m (%)]: 186 (M+), 115 (41), 97 (10), 71 (97), 69 (86), 58 (19), 55 (17), 43 (100), 41 (25).

2$^{nd}$ Isomer:

$^1$H-NMR (200 MHz, CDCl$_3$): δ (ppm) 0.86 (t, J=7.1 Hz, 6H); 1.18-1.74 (m, 9H); 1.31 (s, 3H); 3.24 (ddd, J=2.1 Hz, J=5 Hz, J=11.4 Hz, 1H); 3.38 (dt, J=3 Hz, J=12 Hz, 1H); 3.95 (ddd, J=1.9 Hz, J=5 Hz, J=11.9 Hz, 1H).

$^{13}$C-NMR (50 MHz, CDCl$_3$): δ (ppm) 11.44 & 44.59; 21.58; 25.39; 40.81; 42.91; 45.71; 65.55; 69.27; 77.02.

MS [e/m (%)]: 186 (M+), 115 (34), 71 (87), 69 (71), 58 (13), 55 (15), 43 (100), 41 (23).

Example 2: Preparation of 2-(1-ethyl-propyl)-4-methyl-tetrahydro-2H-pyran-4-ol

The compound is prepared by treating 2-ethylbutyraldehyde and 3-methyl-3-buten-1-ol with a 2 molar equivalent 85:15 mixture of acetic acid/trifluoroacetic acid. The resulting mixture is then treated by KOH in refluxing ethanol to give the pyranol.

Characterization: as Example 1.

Example 3: 4-Methylene-2-(pentan-3-yl)-tetrahydro-2H-pyran (II-Aa), 4-methyl-2-(pentan-3-yl)-5,6-dihydro-2H-pyran (II-Ab) et 4-methyl-2-(pentan-3-yl)-3,6-dihydro-2H-pyran (II-Ac)

Method A:

The compound is prepared by dehydration of the corresponding pyranol (Example 1) in the presence of catalytic amount of PTSA in refluxing toluene, using a Dean-Stark apparatus.

Method B:

The compound is also directly prepared by refluxing a toluene solution of 2-ethylbutyraldehyde (1 mol) and 3-methyl-3-buten-1-ol with catalytic amount of an acid. After completion of the reaction, the reaction mixture is cooled down, washed with saturated aqueous sodium bicarbonate solution and with brine. The organic phase is dried over magnesium sulphate and filtrated. The solvents are evaporated and the crude product is purified by distillation. The different results for method B are summarised in the table below.

| Entry | [Ald.] (mol.l$^{-1}$) | Alcohol | Acid | Time | Bp | Recovered mass | Purity | Isomers ratio (a:b:c) | Yield |
|---|---|---|---|---|---|---|---|---|---|
| 1 | 2M | 2 mol | PTSA (5% weight) | 3.5 hrs | 105-108° C./ 4.4 kPa | 90.5 g | 91% | 60:17:23 | 51% |
| 2 | 2M | 2 mol | PTSA (5% weight) | 3.5 hrs | 73-75° C./ 800 Pa | 132 g | 83% | 54:18:28 | 65% |

-continued

| Entry | [Ald.] (mol.l$^{-1}$) | Alcohol | Acid | Time | Bp | Recovered mass | Purity | Isomers ratio (a:b:c) | Yield |
|---|---|---|---|---|---|---|---|---|---|
| 3 | 3M | 2 mol | PTSA (5% weight) | 12 days | 74° C./ 800 Pa | 89 g | 89% | 5:21:79 | 45% |
| 4 | 3M | 1.5 mol | H$_2$SO$_4$ (5% weight) | 2 days | 78° C./ 800 Pa | 82 g | 84% | 3:13:94 | 41% |
| 5 | 3M | 1 mol | H$_2$SO$_4$ (2% weight) | 2 days | 92° C. 2.0 kPa | 67 g | 98% | 9:18:73 | 40% |
| 6[(*)] | 1M | 1.2 mol | PTSA (2% weight) | 1 day | 94-96° C./ 2.3 kPa | 116 g | 88% | 3:21:76 | 61% |

[(*)]The 3-methyl-3-buten-1-ol is added dropwise to the refluxing solution of aldehyde with acid.

The recovered product consists in a mixture of isomers (II-Aa), (II-Ab) and (II-Ac).

Odour: Top notes: green, rosy, metallic, fruity (mango, bergamote) petitgrain, rose oxide, Cologne.

Dry down notes: none.

Fine distillation with a packed column gives very enriched fractions of the different pyrans a, b or c. Especially a and c are obtained as pure compounds.

IR (film, cm$^{-1}$): 887m, 1061m, 1095 s, 1112m, 1379m, 1462m, 1654m, 2846m, 2875s, 2936s, 2962s.

4-Methylene-2-(pentan-3-yl)-tetrahydro-2H-pyran (II-Aa)

$^1$H-NMR (500 MHz, CDCl$_3$): δ (ppm) 0.85 (t, J=7.5 Hz, 3H); 0.86 (t, J=7.4 Hz, 3H); 1.18-1.52 (m, 5H); 2.01 (t, J=12.2 Hz, 1H); 2.09 (dd br, J=0.8 Hz, J=13.3 Hz, 1H); 2.15 (d br, J=13.1 Hz, 1H); 2.25 (dt, J=5.6 Hz, J=12.8 Hz, 1H); 3.16 (ddd, J=2.2 Hz, J=5.5 Hz, J=11.2 Hz, 1H); 3.30 (ddd, J=2.5 Hz, J=10.5 Hz, J=11.5 Hz, 1H); 4.04 (dd, J=5.6 Hz, J=10.8 Hz, 1H); 4.68 (s, 2H).

$^{13}$C-NMR (125 MHz, CDCl$_3$): δ (ppm) 11.4; 21.4 & 21.5; 35.4; 37.8; 45.8; 68.9; 80.5; 108.1; 145.4.

MS [e/m (%)]: 168 (M+, 4), 97(100), 96(30), 69(19), 68(21), 67(54), 55(16), 53(16), 43(16), 41(28).

Odour: Green (parsley), fruity (pear, green pear peel), rose oxide, petitgrain.

4-Methyl-2-(pentan-3-yl)-5,6-dihydro-2H-pyran (II-Ab)

$^1$H-NMR (500 MHz, CDCl$_3$): δ (ppm) 0.87 (d, J=7.5 Hz, 3H); 0.87 (t, J=6.0 Hz, 3H); 1.18-1.52 (m, 5H); 1.67 (s, 3H); 1.79 (dt, J=5.5 Hz, J=13.1 Hz, 1H); 2.16-2.24 (m, 1H); 3.55 (dt, J=3.6 Hz, J=10.9 Hz, 1H); 3.96 (ddd, J=1.3 Hz, J=5.9 Hz, J=11.1 Hz, 1H); 4.0-41 (m, 1H); 5.28 (s, 1H).

$^{13}$C-NMR (125 MHz, CDCl$_3$): δ (ppm) 12.0 & 12.1; 21.9 & 22.3; 23.2; 30.2; 46.2; 64.0; 75.5; 122.7; 132.7.

MS [e/m (%)]: 168 (M+, 1), 97(100), 43(12), 41(16).

4-Methyl-2-(pentan-3-yl)-3,6-dihydro-2H-pyran (II-Ac)

$^1$H-NMR (500 MHz, CDCl$_3$): δ (ppm) 0.87 (t, J=7.5 Hz, 6H); 1.2-1.28 (m, 1H); 1.27-1.35 (m, 1H); 1.35-1.47 (m, 1H); 1.45-1.55 (m, 2H); 1.68 (s, 3H); 1.71-1.78 (m, 1H); 1.97-1.06 (m, 1H); 3.38 (ddd, J=3.3 Hz, J=6.1 Hz, J=10.0 Hz, 1H); 4.11 (q, J=15.8 Hz, 2H); 5.39 (m, 1H).

$^{13}$C-NMR (125 MHz, CDCl$_3$): δ (ppm) 11.2 & 11.3; 21.2 & 21.3; 23.1; 32.9; 45.6; 66.2; 75.4; 119.6; 132.2.

MS [e/m (%)]: 168 (M+, 5), 124(9), 97(62), 71(17), 69(100), 68(48), 67(32), 55(27), 53(17), 43(40), 41(50).

Example 4: 2-(1-ethyl-propyl)-4-methyl-tetrahydro-2H-pyran-4-yl acetate

The compound is prepared by reacting the corresponding pyranol (Example 1) with acetic anhydride at 60° C. for 2-3 hours. The excess acetic anhydride and acetic acid are then removed by distillation under reduced pressure. The so obtained product is diluted in t-butyl methyl ether and the solution is washed with water, with saturated aqueous sodium bicarbonate solution and with brine. After drying over magnesium sulphate, the solvent is removed by evaporation.

The crude product is purified by distillation to give 2-(1-ethyl-propyl)-4-methyl-tetrahydro-2H-pyran-4-yl acetate as a mixture of isomers.

Odour: Top notes: Green, hesperidic, fatty, spicy.

Dry down notes: Woody, spicy (carvi), powdery/sweet (methyl ionone, ambery, vanilla).

Bp=72° C./0.51 torr.

IR (film, cm$^{-1}$): 1020m, 1083m, 1109m, 1144m, 1236s, 1369m, 1464m, 1736s, 2877m, 2935m, 2964s.

1$^{st}$ Isomer:

$^1$H-NMR (200 MHz, CDCl$_3$): δ (ppm) 0.86 (t, J=7.2 Hz, 6H); 1.10-1.65 (m, 7H); 1.61 (s, 3H); 1.86 (dt, J=5.3 Hz, J=12.9 Hz, 2H); 1.7-2.3 (m, 2H); 2.01 (s, 3H); 3.35-3.50 (m, 1H); 3.58 (ddd, J=2.1 Hz, J=11.7 Hz, J=12.5 Hz, 1H); 3.82 (ddd, J=1.2 Hz, J=5.4 Hz, J=11.7 Hz, 1H).

$^{13}$C-NMR (50 MHz, CDCl$_3$): δ (ppm) 11.41 & 11.59; 21.56 & 21.65; 21.63; 22.30; 36.50; 38.35; 45.48; 63.61; 74.25; 79.51; 170.39.

MS [e/m (%)]: 228 (M+), 97 (100), 69 (12), 55 (6), 43 (34), 41 (13).

2$^{nd}$ Isomer:

$^1$H-NMR (200 MHz, CDCl$_3$): δ (ppm) 0.86 (t, J=7.2 Hz, 6H); 1.10-1.65 (m, 7H); 1.51 (s, 3H); 1.7-2.3 (m, 2H); 1.97 (s, 3H); 3.29 (ddd, J=1.6 Hz, J=4.6 Hz, J=11.9 Hz, 1H); 3.35-3.50 (m, 1H); 3.93 (ddd, J=1.7 Hz, J=5.2 Hz, J=12.1 Hz, 1H).

$^{13}$C-NMR (50 MHz, CDCl$_3$): δ (ppm) 11.49 & 11.56; 21.51; 22.48; 26.39; 37.82; 39.85; 45.73; 64.74; 76.06; 80.55; 170.27.

MS [e/m (%)]: idem 1$^{st}$ isomer.

Example 5: Preparation of propionic acid 2-(1-ethyl-propyl)-4-methyl-tetrahydro-2H-pyran-4-yl ester Propionic acid 2-(1-ethyl-propyl)-4-methyl-tetrahydro-pyran-4-yl ester was prepared from the corresponding pyranol (Example 1 or 2) and propionic anhydride according to example 4. It is obtained as a 55:45 mixture of isomers.

Odour: Myrrhe, roasted beans, not powerful.

IR (film, cm-1): 1003w, 1082m, 1109m, 1142m, 1195s, 1257w, 1358w, 1379m, 1464m, 1734s, 2877m, 2938m, 2964s.

Major Isomer:
$^1$H-NMR (200 MHz, CDCl$_3$): δ (ppm) 0.85 (t, J=7.3 Hz, 6H); 1.11 (t, J=7.2 Hz, 3H); 1.15-1.48 (m, 5H); 1.48-1.60 (m, 2H); 1.50 (s, 3H); 1.95-2.05 (m, 1H); 2.15-2.37 (m, 4H); 3.35-3.55 (m, 2H); 3.82 (ddd, 1H, J=1.1 Hz, J=5.5 Hz, J=11.7 Hz).

$^{13}$C-NMR (50 MHz, CDCl$_3$): δ (ppm) 9.38; 11.37 & 11.58; 21.51; 26.44; 28.86; 36.54; 38.31; 45.45; 63.64; 74.17; 79.17; 173.66.

MS [e/m (%)]: 242 (M+), 169 (2), 168 (2), 153 (2), 140 (5), 97 (100), 69 (15), 57 (17), 43 (43), 41 (13).

Minor Isomer:
$^1$H-NMR (200 MHz, CDCl$_3$, selected data): δ (ppm) 1.07 (t, J=7.0 Hz, 3H); 1.61 (s, 3H); 1.82 (dt, J=5.2 Hz, J=12.7 Hz, 2H); 2.05-2.15 (m, 2H); 2.15-2.3 (m, 1H); 3.22-3.5 (m, 1H); 3.55-3.65 (m, 1H); 3.93 (ddd, 1H, J=1.5 Hz, J=5.1 Hz, J=11.8 Hz).

$^{13}$C-NMR (50 MHz, CDCl$_3$): δ (ppm) 9.12; 11.46 & 11.53; 21.47 & 21.61; 21.69; 28.71; 37.86; 39.86; 45.71; 64.75; 76.05; 80.24; 173.66.

MS [e/m (%)]: idem major isomer.

Example 6: Preparation of but-2-enoic acid 2-(1-ethyl-propyl)-4-methyl-tetrahydro-2H-pyran-4-yl ester and but-3-enoic acid 2-(1-ethyl-propyl)-4-methyl-tetrahydro-2H-pyran-4-yl ester The esters are prepared from the corresponding pyranol (Example 1 or 2) and crotonic anhydride according to example 4. They are obtained as a 80:20 mixture of isomers and can be separated by fine distillation.

Odour: coffee, green nuts, spicy (fenugrec, liveche).

IR (film, cm-1): 970m, 997m, 1060w, 1083m, 1104m, 1142m, 1188s, 1255m, 1295m, 1315m, 1379m, 1446m, 1462m, 1657m, 1717s, 2876m, 2935m, 2963s.

But-2-enoic acid 2-(1-ethyl-propyl)-4-methyl-tetrahydro-2H-pyran-4-yl ester

The compound is obtained as a 95:5 E/Z mixture of enantiomers (ratio of cis/trans isomers:50:50).

Isomer 1 (E-Isomer):
$^1$H-NMR (200 MHz, CDCl$_3$): δ (ppm) 0.84 (t, J=7.2 Hz, 6H); 1.10-1.67 (m, 7H); 1.52 (s, 3H); 1.85 (dd, J=1.7 Hz, J=6.9 Hz, 3H); 1.97-2.13 (m, 1H); 2.13-2.32 (m, 1H); 3.35-3.52 (m, 1H); 3.59 (dt, J=2.0 Hz, J=12.5 Hz, 1H); 3.81 (dd, 1H, J=4.7 Hz, J=11.6 Hz); 5.79 (qd, J=1.6 Hz, J=15.5 Hz, 1H); 6.88 (qd, J=6.9 Hz, J=15.4 Hz, 1H).

$^{13}$C-NMR (50 MHz, CDCl$_3$): δ (ppm) 11.38 & 11.59; 17.81; 21.51 (2C); 26.48; 36.57; 38.46; 45.46; 63.62; 74.19; 79.17; 124.11; 143.63; 165.61.

Isomer 2 (E-Isomer):
$^1$H-NMR (200 MHz, CDCl$_3$): δ (ppm) 0.85 (t, J=7.2 Hz, 6H); 1.10-1.55 (m, 6H); 1.64 (s, 3H); 1.83 (dd, J=1.7 Hz, J=6.9 Hz, 3H); 1.76-1.96 (m, 1H); 1.98-2.15 (m, 2H); 3.30 (ddd, J=1.5 Hz, J=4.5 Hz, J=11.9 Hz, 1H); 3.44 (dt, J=2.3 Hz, J=12.4 Hz, 1H); 3.93 (ddd, J=1.5 Hz, J=5.2 Hz, J=11.9 Hz, 1H); 5.75 (qd, J=1.5 Hz, J=15.4 Hz, 1H); 6.86 (qd, J=6.9 Hz, J=15.5 Hz, 1H).

$^{13}$C-NMR (50 MHz, CDCl$_3$): δ (ppm) 11.47 & 11.54; 17.74; 21.48 & 21.62; 21.71; 31.90; 39.87; 45.71; 64.74; 76.04; 80.26; 124.20; 143.56; 165.62.

MS [e/m (%)]: (isomer 1 (Z or E)) 254 (M+, <1), 168 (2), 153 (2), 140 (6), 97 (100), 69 (34), 55 (6), 43 (13), 41 (21).

MS [e/m (%)]: (isomer 2 (Z or E)) 254 (M+, <1), 97 (100), 69 (33), 55 (5), 43 (12), 41 (17).

But-3-enoic acid 2-(1-ethyl-propyl)-4-methyl-tetrahydro-2H-pyran-4-yl ester

The compound is obtained as a 20:80 mixture of enantiomers.

Minor Isomers:
$^1$H-NMR (200 MHz, CDCl$_3$): δ (ppm) 0.84 (t, 6H, J=7.2 Hz); 1.10-1.25 (m, 3H); 1.25-1.70 (m, 3H); 1.50 (s, 3H); 1.94 (d, 1H, J=7.3 Hz); 2.0-2.35 (m, 2H); 3.04 (td, 2H, J=1.4 Hz, J=7.1 Hz); 5.07-5.12 (m, 1H); 5.15-5.22 (m, 1H); 5.80-6.02 (m, 1H).

$^{13}$C-NMR (50 MHz, CDCl$_3$): δ (ppm) 11.35 & 11.53; 21.47; 26.38; 36.44; 38.23; 40.58; 45.40; 63.54; 74.05; 79.89; 118.37; 130.56; 170.58.

MS [e/m (%)]: 254 (M+, <1), 163 (13), 97 (100), 69 (53), 55 (8), 43 (15), 41 (32).

Major Isomers:
$^1$H-NMR (200 MHz, CDCl$_3$): δ (ppm) 0.85 (t, J=7.2 Hz, 6H); 1.10-1.55 (m, 6H); 1.61 (s, 3H); 1.76-1.96 (m, 1H); 1.98-2.31 (m, 2H); 3.0 (td, J=1.4 Hz, J=7.0 Hz, 2H); 3.22-3.40 (m, 1H); 3.40-3.52 (m, 1H); 3.87-3.99 (m, 1H); 5.05-5.21 (m, 2H); 5.80-6.02 (m, 1H).

$^{13}$C-NMR (50 MHz, CDCl$_3$): δ (ppm) 11.44 & 11.53; 21.60 & 21.66; 26.48; 37.78; 39.79; 40.32; 45.68; 64.71; 76.03; 80.94; 118.16; 130.62; 170.60.

MS [e/m (%)]: idem minor.

Example 7: 2-(1-ethyl-propyl)-4-methyl-tetrahydro-2H-pyran

The compound is prepared by hydrogenation, in the presence of Pd on charcoal, of the corresponding mixture of pyrans (Example 3). It consists in a mixture of two diastereoisomers: cis/trans (72:28).

Odour: Top notes: minty, cocoa powder, musky.

Dry down notes: musky, dusty.

Bp=76-78° C./1.5 kPa.

Cis-Isomer:
$^1$H-NMR (CDCl$_3$, 200 MHz): δ (ppm) 0.80-0.95 (m, 9H); 1.10-1.70 (m, 9H); 3.18 (ddd, 1H, J=1.2 Hz, J=3.28 Hz, J=11.1 Hz); 3.35 (td, 1H, J=2.1 Hz, J=11.8 Hz); 3.97 (ddd, 1H, J=1.2 Hz, J=4.5 Hz, J=11.3 Hz).

$^{13}$C-NMR (CDCl$_3$, 50 MHz): δ (ppm) 11.64, 21.67 & 21.76, 22.57, 30.67, 35.04, 36.98, 46.14, 68.32, 79.30.

Trans-Isomer:
$^1$H-NMR (CDCl$_3$, 200 MHz, selected data): δ (ppm) 1.04 (d, 3H, J=7.1 Hz); 1.65-1.90 (m, 2H); 1.92-2.12 (m, 1H); 3.40-3.95 (m, 3H).

$^{13}$C-NMR (CDCl$_3$, 50 MHz): δ (ppm) 11.24 & 11.27, 18.44, 21.29 & 21.47, 25.02, 32.33, 34.10, 44.47, 62.92, 73.55.

IR (film, cm$^{-1}$): 1082s, 1097s, 1174m, 1458m, 2840s, 2874s, 2928s, 2959s.

MS [e/m (%)]: (cis) 170(M+), 169(1), 99(100), 81(15), 55(22), 43(35), 41(16).

MS [e/m (%)]: (trans) ibid.

Example 8: Preparation of 4-methyl-2-(1-pentyl)-tetrahydro-2H-pyran-4-ol

The compound is prepared from hexanal and 3-methyl-3-buten-1-ol according to example 1. It is obtained as a mixture of isomers.

Odour: Top notes: Green (grass, violet leaves), fruity (apple, pineapple), rosy.

Dry down notes: more floral (jasminic, rosy), fruity.

IR (film, cm$^{-1}$): 1087m, 1111s, 1173m, 1259m, 1378m, 1463m, 2861s, 2933s, 2958s, 3431m (br).

Major Isomer:

$^1$H-NMR (200 MHz, CDCl$_3$): δ (ppm) 0.85 (t, J=6.4 Hz, 3H); 1.2-1.8 (m, 12H); 1.21 (s, 3H); 3.39 (dt, J=2.9 Hz, J=12.0 Hz, 1H); 3.50-3.65 (m, 1H); 3.75-3.87 (m, 1H).

$^{13}$C-NMR (50 MHz, CDCl$_3$): δ (ppm) 13.99; 22.56; 25.14; 31.76; 31.89; 36.14; 38.71; 44.63; 63.56; 67.82; 72.92.

MS [e/m (%)]: 186 (M+), 115 (28), 112 (23), 97 (21), 83 (22), 71 (90), 69 (71), 58 (31), 55 (26), 43 (100), 41 (31).

Minor Isomer:

$^1$H-NMR (200 MHz, CDCl$_3$, selected data): δ (ppm) 1.29 (s, 3H); 3.17-3.32 (m, 1H); 3.72 (dt, J=2.4 Hz, J=11.5 Hz, 1H); 3.93 (ddd, J=1.8 Hz, J=5.0 Hz, J=11.9 Hz, 1H).

$^{13}$C-NMR (50 MHz, CDCl$_3$): δ (ppm) 13.99; 22.56; 25.17; 25.38; 31.83; 36.30; 40.63; 46.57; 65.35; 68.82; 75.87.

MS [e/m (%)]: 186 (M+), 115 (38), 71 (92), 69 (68), 58 (25), 55 (20), 43 (100), 41 (27).

Example 9: Preparation of 4-methylene-2-(1-pentyl)-tetrahydro-2H-pyran (II-Ba), 4-methyl-6-(1-pentyl)-3,6-dihydro-2H-pyran (II-Bb) and 4-methyl-2-(1-pentyl)-3,6-dihydro-2H-pyran (II-Bc)

A (4:33:63) mixture of 4-methylene-2-pentyl-tetrahydro-pyran (II-Ba), 4-methyl-6-pentyl-3,6-dihydro-2H-pyran (II-Bb) and 4-methyl-2-pentyl-3,6-dihydro-2H-pyran (II-Bc) is obtained from 3-methyl-3-buten-1-ol and hexanal according to example 3 (Method B, specific conditions according to entry 6). The isomers can be separated by fine distillation.

Odour: Top notes: Hesperidic (petitgrain, mandarine), green, rosy, metallic.

Dry down notes: Powerful, green, hesperidic, floral, rosy, celery.

IR (film, cm$^{-1}$): 1110m, 1140m, 1381m, 1457m, 2858m, 2931s, 2959s.

4-methylene-2-(1-pentyl)-tetrahydro-2H-pyran (II-Ba)

$^1$H-NMR (200 MHz, CDCl$_3$, selected data): δ (ppm) 4.69 (m, 2H).

$^{13}$C-NMR (50 MHz, CDCl$_3$, selected data): δ (ppm) 68.65, 78.83, 108.1.

4-methyl-6-(1-pentyl)-3,6-dihydro-2H-pyran (II-Bb)

$^1$H-NMR (200 MHz, CDCl$_3$): δ (ppm) 0.87 (t, J=6.3 Hz, 3H), 1.2-1.6 (m, 8H), 1.67 (br s, 3H), 2.0-2.4 (m, 2H), 3.59 (ddd, J=4.0 Hz, J=10.1 Hz, J=11.2 Hz, 1H), 3.97 (ddd, J=2.3 Hz, J=5.9 Hz, J=11.1 Hz, 2H), 5.28-5.34 (m, 1H).

$^{13}$C-NMR (50 MHz, CDCl$_3$): δ (ppm) 14.03, 23.12, 25.03, 30.10, 31.95, 35.67, 35.92, 63.51, 74.03, 124.16, 132.01.

4-methyl-2-(1-pentyl)-3,6-dihydro-2H-pyran (II-Bc)

$^1$H-NMR (200 MHz, CDCl$_3$): δ (ppm) 0.88 (t, J=6.3 Hz, 3H), 1.2-1.6 (m, 8H), 1.67 (br s, 3H), 1.65-2.0 (m, 2H), 3.32-3.51 (m, 1H), 4.05-4.15 (m, 2H), 5.34-5.43 (m, 1H).

$^{13}$C-NMR (50 MHz, CDCl$_3$): δ (ppm) 14.03, 22.61, 22.96, 25.16, 31.91, 395.92 (2C), 65.86, 73.78, 119.71, 131.81.

MS [e/m (%)]: (II-Ba) 168 (M+, 2), 97 (100), 68 (35), 67 (81), 55 (21), 53 (19), 41 (29).

(II-Bb) 168 (M+), 167 (1), 153 (3), 112 (12), 97 (100), 55 (10), 43 (14), 41 (21).

(II-Bc) 168 (M+, 12), 99 (17), 97 (44), 71 (40), 69 (79), 68 (100), 67 (61), 56 (18), 55 (38), 53 (26), 43 (29), 41 (67), 39 (23).

Example 10: Preparation of acetic acid 4-methyl-2-(1-pentyl)-tetrahydro-2H-pyran-4-yl ester The compound is prepared by treating the corresponding pyranol (example 8) with acetic anhydride, according to example 4. It is obtained as a 80:20 mixture of isomers.

Odour: Top notes: Green, woody, spicy.

Dry down notes: Fruity (rhubarb), floral (violet), woody-ambery-spicy (TIMBEROL®, TRIMOFIX®).

IR (film, cm$^{-1}$): 606w, 808w, 940w, 1019m, 1045w, 1087m, 1112m, 1145m, 1183m, 1203w, 1238s, 1369m, 1437w, 1462m, 1737s, 2861m, 2932s, 2957s.

Major Isomer:

$^1$H-NMR (200 MHz, CDCl$_3$): δ (ppm) 0.84 (t, J=6.5 Hz, 3H); 1.08-1.60 (m, 10H); 1.45 (s, 3H); 1.98 (s, 3H); 2.07-2.25 (m, 2H); 3.33-3.48 (m, 1H); 3.56 (dt, J=2.0 Hz, J=12.5 Hz, 1H); 3.70-3.80 (m, H).

$^{13}$C-NMR (50 MHz, CDCl$_3$): δ (ppm) 19.95; 22.24; 22.51; 25.05; 26.13; 31.86; 35.96; 36.20; 42.02; 63.31; 72.72; 79.18; 170.29.

Minor Isomer:

$^1$H-NMR (200 MHz, CDCl$_3$, selected data): δ (ppm) 1.60-1.70 (m, 1H); 1.75-1.90 (m, 1H); 1.93 (s, 3H); 3.77-3.83 (m, 1H).

$^{13}$C-NMR (50 MHz, CDCl$_3$): δ (ppm) 19.95; 22.24; 22.51; 25.11; 31.71; 31.86; 36.14; 38.69; 44.62; 63.54; 72.84; 79.97; 170.16.

Example 11: Fragrance Composition Containing the Pyranol Obtained in Example 1

A Lily of the valley type accord is prepared from the following ingredients:

|  | A | B |
| --- | --- | --- |
| NERYL ACETATE | 30 | 30 |
| BENZYL ACETATE | 10 | 10 |
| CITRONELLYL ACETATE | 16 | 16 |
| GERANYL ACETATE | 50 | 50 |
| STYRALLYL ACETATE | 5 | 5 |
| BENZYLIQUE ALCOHOL | 30 | 30 |
| PHENYLETHYL ALCOHOL | 50 | 50 |
| STYRALLIQUE ALCOHOL | 3 | 3 |
| HEXYLCINNAMIQUE ALDEHYDE | 90 | 90 |
| CYCLAMEN ALDEHYDE | 17 | 17 |
| PEONILE | 67 | 67 |
| CASSIS BASE 345F | 25 | 25 |
| CITRONELLOL PUR BBA | 60 | 60 |
| DIHYDROMYRCENOL | 50 | 50 |
| DIMETOL | 12 | 12 |
| ETHYL LINALOL | 25 | 25 |
| PENTALIDE | 12 | 12 |

| | A | B |
|---|---|---|
| METHYL DIHYDROJASMONATE | 50 | 50 |
| HELIONAL | 50 | 50 |
| LILIAL | 70 | 70 |
| MUSC T | 10 | 10 |
| ORANGE TERPENES | 10 | 10 |
| TERPINEOL BI RECTIFIE | 25 | 25 |
| VERDENOL | 8 | 8 |
| AMBRETTOLIDE | 2 | 2 |
| EUCALYPTOL | 1 | 1 |
| HELIOTROPINE | 3 | 3 |
| HEXENOL CIS 3 | 3 | 3 |
| LINALOL | 16 | 16 |
| DPG | 0 | 200 |
| Pyranol (Example 1) | 200 | 0 |
| TOTAL | 1000 | 1000 |

These 2 compositions (A, B), containing (A) or not (B) the pyranol from example 1, were used in a textile softener at usual dilution, known to the person of the art. The addition of the pyranol in formula A increases considerably the tenacity of the perfume on dried textiles. It brings a more floral-green note, very natural, imparting a fresher sensation to the textile.

Example 12: Fragrance Composition Containing the Pyranol Obtained in Example 1

A Lily of the valley type accord, respecting hypoallergenic constraints, is prepared from the following ingredients:

| | |
|---|---|
| PHENYLETHYL ALCOHOL PURISSIME | 180 |
| DIMETHYLPHENYLETHYLCARBINOL | 26 |
| METHYL DIHYDROJASMONATE | 490 |
| INDOL | 3 |
| IONONE ALPHA | 10 |
| TERPINEOL DROIT CRISTALLISE VMF | 15 |
| HEXYL ACETATE | 4 |
| ALDEHYDE C12 LAURIQUE 10% TEC | 2 |
| HEXENYL CIS 3 ACETATE | 1 |
| STYRALLYL ACETATE | 1 |
| FLORHYDRAL | 3 |
| CITRONELLYLOXYACETALDEHYDE | 5 |
| FLORALOZONE | 5 |
| PHENYLACETIQUE GLYCEROACETAL | 7 |
| UNDECAVERTOL | 2 |
| VELOUTONE | 1 |
| POLYSANTOL | 3 |
| CINNAMYL ACETATE | 2 |
| PHENYLETHYL ACETATE | 3 |
| INDOLAROME | 1 |
| DUPICAL | 5 |
| DPG | 131 |
| Pyranol (Example 1) | 100 |
| TOTAL | 1000 |

Adding the pyranol to the formula brings power to the fragrance and confers to the accord a nice greener, floral, Lily of the valley note.

What is claimed is:

1. A compound having a formula:

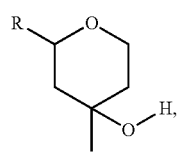

(I)

wherein R is selected from the group consisting of 1 (ethyl-propyl), 1-(2-methyl-butyl), 2-(2-methyl-butyl), 2-(3-methyl-butyl), 1-(3-methyl-butyl), and 1-(2,2-dimethyl)-propyl.

2. The compound according to claim 1, wherein said compound is 2-(1-ethyl-propyl)-4-methyl-tetrahydro-2H-pyran-4-ol.

3. A fragrant agent or a flavoring agent comprising the compound of claim 1 and an acceptable fragrant agent or flavoring agent carrier.

4. A masking agent of odors and/or flavors comprising the compound of claim 1 and an acceptable masking agent carrier.

5. A pharmaceutical, cosmetic, or food composition comprising the compound according to claim 1 in combination with perfuming ingredients, flavoring ingredients, solvents, additives, or fixatives.

* * * * *